US010765608B2

(12) United States Patent
Torres

(10) Patent No.: US 10,765,608 B2
(45) Date of Patent: Sep. 8, 2020

(54) SPRAYABLE COMPOSITIONS FOR STYLING HAIR

(71) Applicant: Manel Torres, London (GB)

(72) Inventor: Manel Torres, London (GB)

( * ) Notice: Subject to any disclaimer, the term of this patent is extended or adjusted under 35 U.S.C. 154(b) by 0 days.

(21) Appl. No.: 16/092,845

(22) PCT Filed: Apr. 15, 2016

(86) PCT No.: PCT/IB2016/000476
§ 371 (c)(1),
(2) Date: Oct. 11, 2018

(87) PCT Pub. No.: WO2017/178855
PCT Pub. Date: Oct. 19, 2017

(65) Prior Publication Data
US 2019/0209445 A1   Jul. 11, 2019

(51) Int. Cl.
A61K 8/04      (2006.01)
A61Q 5/06      (2006.01)
A61K 8/81      (2006.01)
A61K 8/34      (2006.01)
A61K 8/33      (2006.01)
A61K 8/39      (2006.01)

(52) U.S. Cl.
CPC ............... A61K 8/046 (2013.01); A61K 8/33 (2013.01); A61K 8/34 (2013.01); A61K 8/39 (2013.01); A61K 8/8111 (2013.01); A61K 8/8135 (2013.01); A61Q 5/06 (2013.01); A61K 2800/31 (2013.01); A61K 2800/594 (2013.01); A61K 2800/87 (2013.01)

(58) Field of Classification Search
CPC ........ A61K 8/046; A61K 8/8135; A61K 8/34; A61K 8/33; A61K 8/39; A61K 8/8111; A61K 2800/31; A61K 2800/594; A61K 2800/87; A61Q 5/06
See application file for complete search history.

(56) References Cited

U.S. PATENT DOCUMENTS 3,109,761 A * 11/1963 Cobb .................... C06B 45/10
                                                     149/19.4
2004/0170575 A1   9/2004 Belli et al.
2006/0024338 A1   2/2006 Hegedus et al.

FOREIGN PATENT DOCUMENTS

| DE | 2810130 | | 9/1979 |
| DE | 102006058389 | | 6/2008 |
| EP | 1634578 | * | 3/2006 |
| WO | WO 2008/068067 | * | 6/2008 |
| WO | WO 2010035701 | * | 4/2010 |

OTHER PUBLICATIONS

International Search Report, dated Oct. 19, 2017, based on co-pending PCT International Application No. PCT/IB2016/000476—4 Pages.
Written Opinion, dated Oct. 19, 2017, based on co-pending PCT International Application No. PCT/IB2016/000476—7 Pages.

* cited by examiner

Primary Examiner — Shirley V Gembeh
(74) Attorney, Agent, or Firm — McCarter & English, LLP

(57) ABSTRACT

The present invention relates to a sprayable composition for providing a translucent, transparent, semi-transparent or opaque sprayable hair product which exhibits a high level of hold and rigidity to hair such that hair can be held in a particular position for prolonged periods of time without unnatural hardness, superior retention of shape in conditions of heat and humidity, and imparting thickness and body compared to current hairsprays; the composition comprising: a propellant and at least one binder, wherein at least one binder comprises an ethylene vinyl alkanoate copolymer with a weight percent of vinyl alkanoate in the copolymer within the range of 19 wt % to 42 wt %. The invention is also related to the apparatus comprising a container containing the sprayable composition, the methods for forming a coating on a surface and, particularly, the corresponding methods for styling hair, as well as the use of at least one binder in a manufacture of a sprayable composition for styling hair, wherein at least one binder is an ethylene-vinyl alkanoate copolymer with a weight percent of vinyl alkanoate in the copolymer within the range of 19 wt % to 42 wt %.

9 Claims, 4 Drawing Sheets

SPRAYABLE COMPOSITIONS FOR STYLING HAIR

CROSS-REFERENCE TO RELATED APPLICATIONS

This application is a national stage application filed under 35 USC 371 of PCT/IB2016/000476, filed Apr. 15, 2016, which is incorporated herein, in its entirety, by reference.

FIELD OF THE INVENTION

The present invention is aimed at the cosmetic field and mainly directed to a preparation for care of hair. In particular, the invention relates to a sprayable composition for styling scalp and facial hair including decorating eyebrows comprising at least one binder copolymer, which can be used in an aerosol. The invention is also related to an apparatus comprising a container containing the sprayable composition and a device capable of producing a spray of the composition from the container, and to a method for forming a coating on a surface and more particularly a method for styling hair or for decorating eyebrows by spaying the composition of the invention and allowing the propellant, and optionally the solvent, to evaporate.

BACKGROUND

Consumers are frequently seeking to style their scalp or facial hair, for example to provide a certain hairstyle for their scalp hair or, in other cases, style their eyebrows or, in the case of male persons, their beards, moustaches and/or sideburns, by decorating them and, once styled, it is desirable that the hair remains held in the styled position, or conserves a decorated condition. After styling, there is a tendency for hair to return from its styled to its unstyled condition. For example, hair may return to its natural shape if moistened or under high humidity conditions. Therefore, there is a need to provide hair products that retain hair in a styled condition.

Aerosol hairspray products frequently comprise a pressure-resistant container, a valve, a nozzle, a propellant, and a hairstyling formulation. A hairspray formulation is typically ejected from such products via aerosol-forming spraying device. For example, Rollat et al in U.S. Patent Application No. 2006/0110353 relates to a composition for cosmetic treatment of keratin materials, packaged in an aerosol device comprising: (a) at least one propellant and (b) a hairstyling composition comprising at least one polyurethane having a number-average molecular weight ranging from 400 000 to 5 000 000 g/mol, in a cosmetically acceptable medium comprising water.

Another example, Gringore et al in U.S. Patent Application No. 2006/0078507 refers to a composition packaged in an aerosol device, containing: at least one propellant; and a hairstyling composition comprising: (i) at least one non-polyurethane anionic or non-ionic fixative polymer and (ii) at least one anionic acrylic associative polymer; wherein at least one propellant is present in an amount greater than 20% by weight relative to the total weight of the composition.

Birkel et al in U.S. Patent Application No. 2013/0068849 relates to an aerosol hairspray product for styling and/or shaping hair wherein the product comprises: a container; a spraying device; a propellant; a hairstyling formulation comprising: (a) at least about 50% water; and (b) from about 0.01% to about 20% of a hairstyling polymer, wherein the hairstyling polymer is selected from the group consisting of: acrylate copolymers of two or more monomers of (meth) acrylic acid or one of their simple esters; acrylate/hydroxyester acrylate copolymers of butyl acrylate, methyl methacrylate, methacrylic acid, ethyl acrylate and hydroxyethyl methacrylate; polyurethane-14/AMP-acrylates polymer blend; and mixtures thereof.

Henkel AG & Co. KGaA in U.S. Pat. No. 9,132,079 refers to agents for treating keratin-containing fibres, in particular human hair, and methods for the use of such agents are provided. The agent includes at least a specific copolymer of the N-vinylpyrrolidone and at least a polymer with structural units derived from maleic acid ester. The agent is contained in a cosmetically acceptable carrier.

However, in spite of the fact that there are many sprayable compositions for styling hair, a problem with many existing products used for "fixing" hair such that it is held in a styled position with e.g. a heated styling comb, after spraying is that they have a tendency to confer an unnatural hardness and shine. They can also be friable, which may result in loss of holding the hair in a styled position when external forces are applied. It is also desirable for hair products to be, in some cases, translucent or transparent such that they are invisible to the human eye when applied to hair, or in other cases, semi-transparent or opaque which may be used for ornamentation or colouring.

The present invention has the objective of providing other additional translucent, transparent, semi-transparent or opaque sprayable hair products, which exhibit a high level of hold to hair such that hair can be held in a particular position for prolonged periods of time and retain a natural matte appearance after styling with e.g. a heated styling comb.

A further problem with many existing products used for "fixing" hair such that it is held in a styled position is that they tend to lose their shape in conditions of high temperature and humidity.

SUMMARY OF THE INVENTION

The present invention yields equal or superior results holding hair in a particular position in conditions of heat and humidity. The present invention also increases hair body and the apparent thickness of the styled hair in comparison to comparable sprayable hair products without imparting shine and resulting in a natural matte appearance of the styled hair.

In a first aspect, this invention provides a sprayable composition comprising a propellant and at least one binder, and optionally a solvent, characterised in that the binder comprises an ethylene-vinyl alkanoate containing copolymer, wherein the weight percent vinyl alkanoate in the copolymer is within the range of 19 wt % to 42 wt %.

In a second aspect, this invention provides an apparatus comprising a container containing the spraying composition according to the first aspect, and a device capable of producing a spray of the sprayable composition from the container.

In a third aspect, this invention provides a method of forming a coating on a surface, the method comprising: (i) spraying a, composition according to the first aspect onto the surface; and (ii) allowing the propellant, and, where present, the solvent, to evaporate. This invention also provides a method for styling hair, the method comprising: (i) spraying a composition according to the first aspect onto hair; (ii) styling the hair; and (iii) allowing the propellant, and, where present, the solvent, to evaporate. In other embodiment, a method for decorating eyebrows is provided, the method comprising: (i) spraying a composition according to the first aspect onto the eyebrows; (ii) decorating the eyebrows; and (iii) allowing the propellant, and, where present, the solvent, to evaporate.

In a fourth aspect, this invention relates to the use of at least one binder in the manufacture of a sprayable composition for styling facial hair or for decorating eyebrows, wherein at least one binder is an ethylene-vinyl alkanoate copolymer with a weight percent of vinyl alkanoate in the copolymer within the range of 19 wt % to 42 wt %.

The sprayable compositions according to the invention are useful mainly as hairsprays or sprays for eyebrow decoration. This is because they, essentially, provide a thin polymeric film coating to each strand of hair, which helps to maintain hair in a position in which it has been styled. This concept is generally known. An advantage of the compositions of the present invention, when used as a hairspray or a spray for eyebrow decoration, is that it provides other stiff but flexible hold to the styled hair. In other words, a high level of rigidity is provided by the sprayable compositions according to the present invention, such that hair can be held in a particular position for prolonged periods of time after styling with e.g. a heated styling comb without imparting an unnatural hardness and shine, which is common for some previously known products. The compositions of the invention also exhibit equal or superior retention of the desired hair styling shape in conditions of heat and humidity in comparison to previously known products, imparts body and increases the apparent thickness of the hair in comparison to known products.

DETAILED DESCRIPTION OF THE INVENTION

Figure 1:
FIG. 1 illustrates the pre-steam treatment look of four hair samples, according to the Example 13. From left to right, the first hair sample was sprayed with the hairspray identified herein as 'Formulation 27', which corresponds to the formulation as listed in the Example 9; the second hair sample was sprayed with the hairspray identified herein as 'Formulation FBC100', which corresponds to the formulation as listed in the Example 11; the third hair sample was sprayed with the hairspray identified herein as 'Studio 2000', which corresponds to the product known as "Studio 2000 System Professional Hairspray"; and the fourth hair sample was sprayed with the hairspray identified herein as 'L'Oréal Elnett', which corresponds to the product known as "L'Oréal Paris Elnett Flexible Hold".

Embodiments and aspects described herein may comprise or be combinable with elements or components of other embodiments and/or aspects despite not being expressly exemplified in combination, unless otherwise stated or an incompatibility is stated. Moreover, all percentages are by weight of the total composition/formulation, unless stated otherwise. All ranges are inclusive and combinable.

The term "molecular weight" as used herein means the weight average molecular weight unless otherwise stated. The term "polymer" as used herein shall include all materials made by polymerisation of monomers as well as natural polymers. Polymers made from only one type of monomer are called "homopolymers". The term "copolymer" as used herein refers to a polymer derived from more than one species of monomer. As used herein, the term "vinyl alkanoate" covers vinyl acetate (VA), vinyl propionate, vinyl butyrate, vinyl 2-ethyl hexanoate, or suitable mixtures thereof. Similarly, the term "ethylene vinyl alkanoate copolymer" covers: ethylene vinyl acetate copolymer, ethylene vinyl propionate copolymer, ethylene vinyl butyrate copolymer, ethylene vinyl 2-ethyl haxanoate copolymer, or suitable mixtures thereof.

Herein, the term "hair" refers to a protein filament that grows from follicles found in the dermis, or skin. It can grow on most external areas of the human body, such as head or face. The term "hair" as used herein thus includes human scalp hair, eyebrow hair, moustache hair, sideburn hair and beard hair.

The terms "style", "styled" and "styling" as used herein refer to putting hair into a desired position to provide a hairstyle or hairdo to the scalp hair and includes, especially in the case of eyebrows, beards and sideburns, providing a decoration thereto.

Herein, "comprising" means that other steps and other ingredients which do not affect the end result can be added. This term encompasses the terms "consisting of" and "consisting essentially of". The compositions, methods, uses, and processes herein can comprise, consist of, and consist essentially of the elements and limitations of the invention described herein, as well as any of the additional or optional ingredients, components, steps, or limitations described herein.

According to the first aspect of the invention, the sprayable compositions comprise at least one binder. That binder may be an ethylene-vinyl alkanoate containing copolymer.

According to this aspect, the total amount of binder is within the range of 1 wt % to 10 wt %. Preferably, the total amount of binder is within the range of 1 wt % to 5 wt %. The presence of a low amount of binder results in the sprayable composition having a translucent effect on the surface on which it is sprayed. In other words, the sprayable composition results in a substantially translucent or transparent coating. It is preferred that at least one binder is a random copolymer of vinyl acetate monomers.

Preferably, at least one binder has a vinyl alkanoate content within the range of 19 wt % to 42 wt %, preferably the vinyl alkanoate content is within the range of 35 wt % to 42 wt %, and more preferably within the range of 40 wt % to 42 wt %.

Moreover, the sprayable compositions of the invention may comprise at least two binders. In this aspect of the invention, the first and second binders may be selected from ethylene-vinyl alkanoate containing copolymers or may be selected from an ethylene-vinyl alkanoate containing copolymer and a homopolymer of vinyl alkanoate. However, it is preferred that the first binder is an ethylene-vinyl alkanoate containing copolymer, and the second binder is selected from a homopolymer of vinyl alkanoate, such as polyvinylacetate (PVA), due to substantial hair hold.

The total amount of at least two binders in the sprayable composition is within the range of 1 wt % to 10 wt %, and preferably, the total amount of binder is within the range of 1 wt % to 5 wt %.

In this embodiment of the invention, the first binder may be a random copolymer of ethylene and vinyl acetate with a weight percent of vinyl acetate in the copolymer within the range of 19 wt % to 42 wt %, more preferably within the range of about 35 wt % to 42 wt %, more preferably within the range of 39 wt % to 42 wt %, and more preferably within the range of 40 wt % to 42 wt %, and the second binder may be a polyvinylacetate (PVA) 500000 MW.

When the sprayable compositions of the invention comprise an ethylene-vinyl alkanoate containing copolymer as first and/or second binder, said binder(s) may have a Melt Flow Rate (190° C./2.16 kg) within the range of about 2.5 g/10 min to 900 g/10 min, more preferably within the range of about 48 g/10 min to 85 g/10 min (ISO 1133/ASTM D1238).

Two of the preferred ethylene vinyl acetate copolymers used as binders are commercially available from DuPont and Arkema Companies, and are known as Elvax grade 40W and Evatane 42-60, respectively. Evatane 42-60 is a random copolymer of ethylene and vinyl acetate with a VA content of more than 41 wt % with a Melt Flow Rate (190° C./2.16 kg) within the range of about 65 to 85 g/10 min (ISO 1133/ASTM D1238), a density (23° C.) of 0.96 g/cm$^3$, a melting point of 48° C., a Vicat softening point (10 N) of less than 40° C., a ring & ball temperature of 95° C., an elongation at break of 900-1100%, a tensile straight at break of 5 MPa, and a hardness Shore A of 42. On the other hand, Elvax 40W is an ethylene vinyl acetate copolymer resin in pellet form with 39 to 42 wt % vinyl-acetate co-monomer with a Melt Flow Rate (190° C./2.16 kg) within the range of about 48-66 g/10 min (ISO 1133/ASTM D1238), a density of 0.965 g/cm$^3$, a melting point (DSC) of 47° C. (117° F.), a freezing point (DSC) of 27° C. (81° F.), an inherent viscosity of 0.70 g/ml, a hardness of 40 shore, and a softening point of 104° C.

The key functions that the ethylene-vinyl alkanoate containing copolymers provide when present in the compositions of the present invention is the formation of a very fine translucent or transparent film on the surface of the hair from root to tip. The formation of the fine film occurs due to that the film is comprised of miniscule droplets of formulation adhering to each other from the surfaces of individual hairs. This provides excellent hold and an appearance of increased volume while maintaining a natural look and feel. Used in the sprayable compositions of the present invention, e.g. neither Evatane 42-60 nor Elvax 40W are visible to the bare human eye, they are not hard and they provide elasticity to the translucent film, permitting e.g. easy hair styling.

In contrast to the binders of the present invention, polymers such as linear block copolymers based on styrene and butadiene with bound styrene of 31% mass (i.e. Kraton D1101 ASM) or Elvax 40L03 did not provide sufficient functions and characteristics to be used in the sprayable compositions of the invention. In the case of Kraton D1101 ASM, it is white in colour, and even after being dissolved and sprayed, it retains its whiteness, which is not a desired characteristic in the sprayable compositions of the present invention. As for Elvax 40L03, it did partially provide a similar effect of a translucent hair product to Evatane 42-60 and Elvax 40W, however, an unwanted characteristic of Elvax 40L03 used in the compositions of the invention caused the aerosol can to spit out short white strings of polymeric substance, which may be due to the lack of dissolution of the additives in the Elvax40L03 resin, formation of a side-product, or even the polymer resin itself achieving only a partial dissolution.

Furthermore, the sprayable compositions of the invention may comprise at least three binders. In this aspect of the invention, the first binder may be selected from a copolymer of ethylene-vinyl alkanoate, such as e.g. Evatane 42-60, the second binder may be selected from another copolymer of ethylene-vinyl alkanoate, such as e.g. Elvax 40W, and the third binder may be selected from a homopolymer of vinyl alkanoate, such as e.g. polyvinylacetate (PVA). Typically, the PVA has a molecular weight of about 500,000. According to this aspect, the total amount of the at least three binders is within the range of 1 wt % to 10 wt %, preferably, within the range of 1 wt % to 5 wt %, and more preferably within the range of 1 wt % to 2 wt %.

Generally, the propellant is an organic compound but any suitable propellant can be used.

Suitable propellants include aliphatic hydrocarbons having a low boiling point (so that they are gaseous under ambient pressure conditions at room temperature) such as liquefied petroleum gas (LPG), which is a commercial product comprised mainly of propane and/or butane. It is also possible to use carbon dioxide as a propellant. Alternatively, volatile ethers can be used, such as dimethyl ether. The propellant in the spraying composition can be selected from the group consisting of dimethyl ether, liquefied petroleum gas, or a combination thereof. Preferably, the propellant is dimethyl ether. Dimethyl ether is a particularly preferred propellant because it can act as a solvent for the binder.

Typically, propellants make up between 50 wt % and 99 wt % of the composition, preferably the propellant is present in the sprayable composition in an amount of at least 80 wt %, more preferably of at least 85 wt %, and more preferably of at least 90 wt %.

Preferably, the propellant is present in an amount of at least 80 wt %, preferably at least 85 wt %, more preferably at least 90 wt %.

It is desirable that the binder is soluble in the propellant. Otherwise, the binder may have a tendency to precipitate. This is undesirable since it will lead to inferior results owing to blockage of a nozzle from which the composition is sprayed. It can be envisaged that if there is precipitation, this would not lead to a uniform coating of the surface onto which the composition is sprayed.

The composition of the present invention may comprise fibres. When present, the fibres in the composition should be of a certain minimum length. Generally, at least 80% of the fibres have a length of at least 0.02 mm. Preferably, at least 90%, more preferably at least 95% and most preferably substantially all of the fibres in the composition have a length of at least 0.02 mm.

The fibres of the composition should not be too long since a composition comprising long fibres cannot be sprayed easily because the fibres can block a small nozzle. Generally, at least 80% (by weight) of the fibres have a length not more than 10 mm, preferably not more than 5 mm, more preferably not more than 1 mm, still more preferably not more than 0.5 mm, even more preferably not more than 0.25 mm, most preferably not more than 0.15 mm. Preferably, at least 90%, more preferably at least 95% and most preferably substantially all of the fibres have a length not more than 10 mm, preferably not more than 5 mm, more preferably not more than 1 mm, still more preferably not more than 0.5 mm, even more preferably not more than 0.25 mm, more preferably not more than 0.15 mm, and most preferably not more than 0.02 mm. Preferably, the fibres are milled before use to a length of approximately 0.02-0.15 mm.

Both synthetic and natural fibres may be used in the composition. Examples of fibres which may be used include: cotton fibres or cotton flock, cellulose fibres, wool fibres, silk fibres, Jute fibres or jute flock, acrylic fibre flock (e.g. polyacrylonitrile flock), nylon fibres, viscose flock, cashmere fibres, linen fibres seaweed cellulose fibres, ramie cellulose fibres, mink fur fibres, rabbit hair fibres, aramid fibres, chitosan fibres, other natural fibres, Carbon fibres, Glass fibres, Metallic fibres (e.g., steel, copper, silver etc.), ceramic fibres, and alpaca fibres.

Generally, the fibres in the composition are at least 5, 10, 20, 30 or 40% (by weight of fibres). They may be polymeric fibres or cellulosic fibres.

Preferably, the fibres in the composition are selected from the group consisting of cotton fibres, jute fibres, acrylic fibre flock, polyacrylonitrile flock, nylon and viscose flock.

The sprayable compositions according to the invention may further comprise a solvent. The binder may be soluble in the solvent and the solvent is miscible with the propellant. This is particularly important for a sprayable composition because precipitation of binder can lead to inferior results and may lead to blockage of a nozzle from which the composition is sprayed. Further, it can be envisaged that precipitation of binder will not lead to a uniform coating when sprayed onto a surface.

The solvent of the present invention is, generally, an organic compound. The solvent in the spraying composition can be selected from the group consisting of alcohols, ethers and hydrochlorocarbons. Suitable solvents include alcohols such as methanol or ethanol, preferably ethanol.

Addition of an alcohol to the composition can prevent the composition from being too cold when sprayed. This can be advantageous when the surface to be sprayed is human or animal hair, since it prevents the hair from being "frozen".

The compositions of the invention may comprise further additive components such as adhesives, pigments and dyes, fragrances (i.e. perfumes), emulsifying agents, physiologically active agents, oils, metallic powders/particles, UV-absorbing particles, surfactants, fire retardants, conditioners and waxes.

Suitable conditioners are selected from humectants, sunscreens, moisturisers, acidifiers, lubricants, preservatives and anti-static agents. Preferred metallic powders for imparting colour to the sprayable compositions of the invention may be gold (e.g. superfine gold), silver, copper and bronze powders.

Silicone oil may be added as a lubricant. This can advantageously aid spraying. Almond and argan oils may also be added to the sprayable compositions of the invention, which is advantageous when the sprayable compositions of the invention are used to coat hair, e.g. the composition is a hairspray or a spray for decorating eyebrows.

If different colour coatings are desired then a pigment or dye may be added to the sprayable compositions of the invention.

Cellulose ethers may be added to the compositions, preferably in powder form such as microcrystalline cellulose, methyl cellulose, hydroxyethyl cellulose, hydroxypropyl methyl cellulose and hydroxypropyl cellulose. Preferably, hydroxypropyl methyl cellulose or hydroxypropyl cellulose are used.

Other additional components that may be added to the sprayable compositions of the invention are: triblock copolymers, such as polystyrene triblock copolymers (PSPIPS), polystyrenepolyethylenebutylenepolystyrene (SEBs) polyvinylpyrridone (PVP), oleyl alcohol, poly isobutyl methacrylate, glycerine, Shellac, and other resins and polyurethane diol.

Polyurethane diol is a preferred additive, since it improves fluidity of the composition. It also helps to provide a sprayable composition having an even consistency, i.e. an evenly distributed sprayable composition. Preferably, the amount of polyurethane diol present is in the range of from 5 to 10 wt %, based on the total weight of the composition. More preferably, up to 5 wt % of polyurethane diol is used in order to avoid unwanted "stickiness" of the product.

When fibres are present in the sprayable compositions of the invention, it is important that the additives are selected such that they do not cause aggregation of the fibres. Some agents, e.g. dispersants such as surfactants, in particular organic solvent soluble surfactants may be added to prevent aggregation of fibres in the sprayable compositions of the invention.

The second aspect of the invention relates to an apparatus comprising a container containing a sprayable composition according to the first aspect of the invention and a device capable of producing a spray of the composition from the container. Preferably, the device capable of producing a spray has a nozzle with an internal diameter of 0.05 to 2 mm, more preferably 0.1 to 1 mm.

It is preferred that the container is an aerosol can pressurised to a pressure of above 1 and up to 20 atmospheres, preferably between 3 and 20 atmospheres, more preferably between 4 and 15 atmospheres, more preferably 5 to 10 atmospheres, depending on the particular propellant used. By "aerosol can" we mean a metal container of the type commonly used to store pressurised products e.g. hair spray or deodorant. The propellant is a liquid inside the pressurised container but evaporates on expansion when it is sprayed out.

According to the third aspect of the invention, the compositions according to the invention can be used in a method of forming a coating on a surface. The method comprises spraying a composition of the invention onto a surface and then allowing the propellant (and solvent, if present) to evaporate, thereby leaving a translucent or transparent coating on the surface.

Preferably, the surface to be coated is human or animal hair, such that hair may be styled using a sprayable composition of the invention. For example, after spraying of the composition onto human hair, the hair may be styled before evaporation of the volatile components occurs. This leads to strong hold of the hairstyle that has been created because the coating that is applied provides stiffness to the hair, while still retaining bounciness.

According to the fourth aspect, the invention is related to the use of at least one binder in a manufacture of a sprayable composition for styling hair or for decorating eyebrows, wherein at least one binder is an ethylene-vinyl alkanoate copolymer. The weight percent of vinyl alkanoate in the copolymer is within the range of 19 wt % to 42 wt %. The total amount of binder in the composition is within the range of 1 wt % to 10 wt %, preferably within the range of 1 wt % to 5 wt %, and more preferably within the range of 1 wt % to 2 wt %.

The ethylene-vinyl alkanoate copolymer in the fourth aspect of the invention may be a random copolymer of ethylene and vinyl acetate with a weight percent vinyl acetate in the copolymer within the range of 19 wt % to 42 wt %, preferably within the range of 35 wt % to 42 wt %, and preferably within the range of 40 wt % to 42 wt %. When present a second binder in the sprayable compositions, a homopolymer of vinyl alkanoate, such as polyvinylacetate (PVA) is preferred.

According to the fourth aspect, the propellant may be present in an amount within the range of 80 wt % to 99 wt %, preferably within the range of 85 wt % to 99 wt %, and more preferably within the range of 90 wt % to 99 wt %. The propellant may be selected from dimethyl ether, liquefied petroleum gas, or a combination thereof. It is desired that the propellant is dimethyl ether.

The sprayable composition to be prepared according to the fourth aspect of the invention may further comprise a solvent, an additive and fibres. Where present, the solvent is selected from the group consisting of alcohols, ethers and hydrochlorocarbons. Preferably the solvent is an alcohol selected from the group consisting of methanol or ethanol. Where present, the additive is selected from the group consisting of dyes, oils, perfumes, surfactants, fire retardants, metal powders/particles such as copper, silver and gold, conditioners such as humectants, sunscreen, moisturisers, acidifiers, lubricants, preservatives, anti-static agents, and wax. Where present, at least 80% of the fibres have a length of at least 0.02 mm and not more than 10 mm.

The methods of delivery of the spray composition of the invention may include:
1. Aerosol cans
2. Compressed air spray guns
3. Airbrush guns
4. Portable spray canisters
5. Hand pump sprays
6. Robotic sprayers
7. Pressurised cartridges By way of non-limiting illustration, concrete examples of certain embodiments of the present disclosure are given below.

EXAMPLES

Compositions according to the following examples were prepared and tested for their ability to produce a translucent, transparent, semi-transparent or opaque coating when sprayed, as well as to exhibit a high level of hold to hair such that hair can be held in a particular position for prolonged periods of time without exhibiting stickiness.

The following formulation incorporates only a binder i.e. a random copolymer of ethylene and vinyl acetate with 19 wt % to 42 wt % vinyl-acetate co-monomer (e.g. Evatane).

Example 1: Semi-Transparent or Opaque Sprayable Composition for Hair Ornamentation

| Component | Ingredient | Quantity (g) | % w/w |
|---|---|---|---|
| Propellant | Dimethyl ether | 75 | 92.5 |
| Binder | A random copolymer of Ethylene and Vinyl acetate with 19 wt % to 42 wt % vinyl-acetate co-monomer (e.g. Evatane) | 2 | 2.5 |
| Additive | Polyurethane diol | 4 | 5 |

Method of preparation: A ball bearing was added into a 200 mL aerosol can followed by a random copolymer of ethylene and vinyl acetate with 19 wt % to 42 wt % vinyl-acetate co-monomer (e.g. Evatane) (2 g) and polyurethane diol (4, g). The aerosol can was crimped and filled with Dimethyl ether (70 g) at 5 bar pressure and a nozzle was attached.

The following are formulations incorporating a second binder (i.e. polyvinyl acetate 500000 MW).

Example 2: Semi-Transparent or Opaque Sprayable Composition for Hair Ornamentation

| Component | Ingredient | Quantity (g) | % w/w |
|---|---|---|---|
| Propellant | Dimethyl ether | 75 | 92.5 |
| Binder | A random copolymer of ethylene and vinyl acetate with 19 wt % to 42 wt % vinyl-acetate co-monomer (e.g. Evatane) | 1 | 1.23 |
| Binder | Polyvinyl acetate 500000 MW | 1 | 1.23 |
| Additive | Polyurethane diol | 4 | 5 |

Method of preparation: A ball bearing was added into a 200 mL aerosol can followed by a random copolymer of ethylene and vinyl acetate with 19 wt % to 42 wt % vinyl-acetate co-monomer (e.g. Evatane) (1 g), polyvinyl acetate 500000 MW (1 g) and polyurethane diol (4 g). The aerosol can was crimped and filled with dimethyl ether (70 g) at 5 bar pressure and a nozzle was attached.

Example 3: Semi-Transparent or Opaque Sprayable Composition for Hair Ornamentation

| Component | Ingredient | Quantity (g) | % w/w |
|---|---|---|---|
| Propellant | Dimethyl ether | 75 | 91.5 |
| Binder | A random copolymer of Ethylene and Vinyl acetate with 19 wt % to 42 wt % vinyl-acetate co-monomer (e.g. Evatane) | 1 | 1.22 |
| Binder | Polyvinyl acetate 500000 MW | 2 | 2.43 |
| Additive | Polyurethane diol | 4 | 4.88 |

Method of preparation: A ball bearing was added into a 200 mL aerosol can followed by a random copolymer of ethylene and vinyl acetate with 19 wt % to 42 wt % vinyl-acetate co-monomer (e.g. Evatane) (1 g), polyvinyl acetate 500000 MW (2 g) and polyurethane diol (4 g). The aerosol can was crimped and filled with dimethyl ether (70 g) at 5 bar pressure and a nozzle was attached.

Example 4: Semi-Transparent or Opaque Sprayable Composition for Hair Ornamentation

| Component | Ingredient | Quantity (g) | % w/w |
|---|---|---|---|
| Propellant | Dimethyl ether | 75 | 90.4 |
| Binder | A random copolymer of Ethylene and Vinyl acetate with 19 wt % to 42 wt % vinyl-acetate co-monomer (e.g. Evatane) | 1 | 1.20 |
| Binder | Polyvinyl acetate 500000 MW | 3 | 3.66 |
| Additive | Polyurethane diol | 4 | 4.82 |

Method of preparation: A ball bearing was added into a 200 mL aerosol can followed by a random copolymer of ethylene and vinyl acetate with 19 wt % to 42 wt % vinyl-acetate co-monomer (e.g. Evatane) (1 g), polyvinyl acetate 500000 MW (3 g) and polyurethane diol (4 g). The aerosol can was crimped and filled with Dimethyl ether (70 g) at 5 bar pressure and a nozzle was attached.

Example 5: Translucent or Transparent Sprayable Composition for Hair Styling

| Component | Ingredient | Quantity (g) | % w/w |
|---|---|---|---|
| Solvent | Ethanol | 9.95 | 12.16-12.18 |
| Propellant/solvent | Dimethyl ether | 70.00 | 85.61-85.75 |
| Binder | Polyvinyl acetate 500000 MW | 0.60 | 0.73 |
| Binder | Ethylene vinyl acetate copolymer resin in pellet form, with 40 wt % vinyl-acetate co-monomer (Elvax 40W) | 0.40-0.50 | 0.49-0.61 |
| Additive | Hydroxypropyl methylcellulose polymer powder (i.e. Methocel 311) | 0.05 | 0.06 |
| Additive | Polyurethane diol | 0.60 | 0.73 |
| Fibres | Cellulose, 20 μm | 0.05 | 0.06 |

Method of preparation: Hydroxypropyl methylcellulose polymer powder (i.e. Methocel 311) (0.05 g) was added slowly into a beaker of ethanol (250 mL) to achieve maximum dispersion and mixed vigorously at 70° C. using a magnetic stirrer-hotplate overnight. A ball bearing was added into a 200 mL aerosol can followed by ethylene vinyl acetate copolymer resin in pellet form with 40 wt % vinyl-acetate co-monomer (Elvax 40W) (0.4-0.5 g), poly(vinyl acetate) 500000 MW (0.6 g) and cellulose (0.05 g, 20 μm). Polyurethane diol solution (0.6 g) was then added dropwise to the aerosol can along with the previously prepared solution of hydroxypropyl methylcellulose polymer powder (i.e. Methocel 311) in ethanol (9.95 g). The aerosol can was crimped and filled with dimethyl ether (70 g) at 5 bar pressure and a nozzle was attached.

Example 6: Translucent or Transparent Sprayable Composition for Hair Styling

| Component | Ingredients | Quantity (g) | % w/w |
|---|---|---|---|
| Solvent | Ethanol | 9.95 | 12.16-14.8 |
| Propellant/solvent | Dimethyl ether | 70.00 | 85.54-85.61 |
| Binder | Polyvinyl acetate 500000 MW | 0.60 | 0.73 |
| Binder | Ethylene vinyl acetate copolymer resin in pellet form, with 40 wt % vinyl-acetate co-monomer (Elvax 40W) | 0.40-0.50 | 0.49-0.611 |
| Additive | Hydroxypropyl methylcellulose polymer powder (i.e. Methocel 311) | 0.05 | 0.06 |
| Additive | Polyurethane diol | 0.60 | 0.73 |
| Fibres | Cellulose, 20 μm | 0.10 | 0.12 |

Method of preparation: Hydroxypropyl methylcellulose polymer powder (i.e. Methocel 311) (0.05 g) was added slowly into a beaker of ethanol (250 mL) to achieve maximum dispersion and mixed vigorously at 70° C. using a magnetic stirrer-hotplate overnight. A ball bearing was added into a 200 mL aerosol can followed by ethylene vinyl acetate copolymer resin in pellet form, with 40 wt % vinyl-acetate co-monomer (Elvax 40W) (0.4-0.5 g), Polyvinyl acetate 500000 MW (0.6 g) and cellulose (0.1 g, 20 μm). Polyurethane diol solution (0.6 g) was then added dropwise to the aerosol can along with the previously prepared solution of hydroxypropyl methylcellulose polymer powder (i.e. Methocel 311) in ethanol (9.95 g). The aerosol can was crimped and filled with dimethyl ether (70 g) at 5 bar pressure and a nozzle was attached.

Example 7: Opaque Sprayable Composition for Hair Colouration or Ornamentation

| Component | Ingredients | Quantity (g) | % w/w |
|---|---|---|---|
| Solvent | Ethanol | 9.95 | 12.09-12.12 |
| Propellant/solvent | Dimethyl ether | 70.00 | 85.12-85.26 |
| Binder | Polyvinyl acetate 500000 MW | 0.60 | 0.73 |
| Binder | Ethylene vinyl acetate copolymer resin in pellet form, with 40 wt % vinyl-acetate co-monomer (Elvax 40W) | 0.40-0.50 | 0.49-0.61 |
| Additive | Hydroxypropyl methylcellulose polymer powder (i.e. Methocel 311) | 0.05 | 0.06 |
| Additive | Polyurethane diol | 0.60 | 0.73 |
| Fibres | Cellulose, 20 μm | 0.05 | 0.06 |
| Dye | Duracet Black BFE Dye | 0.45 | 0.55 |

Method of preparation: Hydroxypropyl methylcellulose polymer powder (i.e. Methocel 311) (0.05 g) was added slowly into a beaker of ethanol (250 mL) to achieve maximum dispersion and mixed vigorously at 70° C. using a magnetic stirrer-hotplate overnight. A ball bearing was added into a 200 mL aerosol can followed by ethylene vinyl acetate copolymer resin in pellet form with 40 wt % vinyl-acetate co-monomer (Elvax 40W) (0.4-0.5 g), polyvinyl acetate 500000 MW (0.6 g), Duracet Black BFE Dye (a mixture of azo dyes available from Franklin International, Columbus, Ohio) (0.45 g) and cellulose (0.05 g, 20 μm). Polyurethane diol solution (0.6 g) was then added dropwise to the aerosol can along with the previously prepared solution of hydroxypropyl methylcellulose polymer powder (i.e. Methocel 311) in ethanol (9.95 g). The aerosol can was crimped and filled with dimethyl ether (70 g) at 5 bar pressure and a nozzle was attached.

Example 8: Opaque Sprayable Composition for Hair Colouration or Ornamentation

| Component | Ingredients | Quantity (g) | % w/w |
|---|---|---|---|
| Solvent | Ethanol | 9.95 | 12.09-12.11 |
| Propellant/solvent | Dimethyl ether | 70.00 | 85.05-85.20 |
| Binder | Polyvinyl acetate 500000 MW | 0.60 | 0.73 |
| Binder | Ethylene vinyl acetate copolymer resin in pellet form, with 40 wt % vinyl-acetate co-monomer (Elvax 40W) | 0.40-0.50 | 0.49-.60 |
| Additive | Hydroxypropyl methylcellulose polymer powder (i.e. Methocel 311) | 0.05 | 0.06 |
| Additive | Polyurethane diol | 0.60 | 0.73 |
| Fibres | Cellulose, 20 μm | 0.10 | 0.12 |
| Dye | Duracet Black BEE Dye | 0.45 | 0.55 |

Method of preparation: Hydroxypropyl methylcellulose polymer powder (i.e. Methocel 311) (0.05 g) was added slowly into a beaker of ethanol (250 mL) to achieve maximum dispersion and mixed vigorously at 70° C. using a magnetic stirrer-hotplate overnight. A ball bearing was added into a 200 mL aerosol can followed by ethylene vinyl acetate copolymer resin in pellet form, with 40 wt % vinyl-acetate co-monomer (Elvax 40W) (0.4-0.5 g), polyvinyl acetate 500000 MW (0.6 g), Duracet black BFE dye (0.45 g) and cellulose (0.1 g, 20 μm). Polyurethane diol solution (0.6 g) was then added dropwise to the aerosol can along with the previously prepared solution of Hydroxypropyl methylcellulose polymer powder (i.e. Methocel 311) in ethanol (9.95 g). The aerosol can was crimped and filled with dimethyl ether (70 g) at 5 bar pressure and a nozzle was attached.

We observed that all formulations of Examples 1 to 8 yielded a spray jet of consistent force and quantity from a nozzle; the resulting coating was thin, and considering the formulation, the coating was translucent, transparent, semi-transparent or opaque. In addition, all formulations of Examples 1 to 8 exhibit a high level of hold and rigidity to hair such that hair can be held in a particular position for prolonged periods of time without unnatural hardness, superior retention of shape in conditions of heat and humidity, and imparting thickness and body compared to current hairsprays.

The following are formulations incorporating a third binder. They work in quantities in the 1-2 g mass range.

Example 9: Translucent or Transparent Sprayable Composition for Hair Styling

| Component | Ingredients | Quantity (g) | % w/w |
|---|---|---|---|
| Solvent | Ethanol | 9.95 | 12.18 |
| Propellant/solvent | Dimethyl ether | 70.00 | 85.68 |
| Binder | Polyvinyl acetate 500000 MW | 0.60 | 0.73 |
| Binder | A random copolymer of Ethylene and Vinyl acetate with a VA content of more than 41 wt % (Evatane 42-60) | 0.10 | 0.12 |
| Additive | Hydroxypropyl methylcellulose polymer powder (i.e. Methocel 311) | 0.05 | 0.06 |
| Additive | Polyurethane diol | 0.60 | 0.73 |
| Fibres | Cellulose, 20 μm | 0.05 | 0.06 |
| Binder | Ethylene vinyl acetate copolymer resin in pellet form, with 40 wt % vinyl-acetate co-monomer (Elvax 40W) | 0.30 | 0.36 |

Method of preparation: Hydroxypropyl methylcellulose polymer powder (i.e. Methocel 311) (0.05 g) was added slowly into a beaker of ethanol (250 mL) to achieve maximum dispersion and mixed vigorously at 70° C. using a magnetic stirrer-hotplate overnight. A ball bearing was added into a 200 mL aerosol can followed by ethylene vinyl acetate copolymer resin in pellet form, with 40 wt % vinyl-acetate co-monomer (Elvax 40W) (0.3 g), a random copolymer of ethylene and vinyl acetate with a vinyl acetate content of more than 41 wt % (Evatane 42-60) (0.1 g), polyvinyl acetate 500000 MW (0.6 g) and cellulose (0.05 g, 20 μm). Polyurethane diol solution (0.6 g) was then added dropwise to the aerosol can along with the previously prepared solution of hydroxypropyl methylcellulose polymer powder (i.e. Methocel 311) in ethanol (9.95 g). The aerosol can was crimped and filled with dimethyl ether (70 g) at 5 bar pressure and a nozzle was attached.

Example 10: Translucent or Transparent Sprayable Composition for Hair Styling

| Component | Ingredients | Quantity (g) | % w/w |
|---|---|---|---|
| Solvent | Ethanol | 9.95 | 12.17 |
| Propellant/solvent | Dimethyl ether | 70.00 | 85.61 |
| Binder | Polyvinyl acetate 500000 MW | 0.60 | 0.73 |
| Binder | A random copolymer of Ethylene and Vinyl acetate with a VA content of more than 41 wt % (Evatane 42-60) | 0.10 | 0.12 |
| Additive | Hydroxypropyl methylcellulose polymer powder (i.e. Methocel 311) | 0.05 | 0.06 |
| Additive | Polyurethane diol | 0.60 | 0.73 |
| Fibres | Cellulose, 20 μm | 0.10 | 0.12 |

-continued

| Component | Ingredients | Quantity (g) | % w/w |
|---|---|---|---|
| Binder | Ethylene vinyl acetate copolymer resin in pellet form, with 40 wt % vinyl-acetate co-monomer (Elvax 40W) | 0.30 | 0.36 |

Method of preparation: Hydroxypropyl methylcellulose polymer powder (i.e. Methocel 311) (0.05 g) was added slowly into a beaker of ethanol (250 mL) to achieve maximum dispersion and mixed vigorously at 70° C. using a magnetic stirrer-hotplate overnight. A ball bearing was added into a 200 mL aerosol can followed by ethylene vinyl acetate copolymer resin in pellet form, with 40 wt % vinyl-acetate co-monomer (Elvax 40W) (0.3 g), a random copolymer of Ethylene and Vinyl acetate with a vinyl acetate content of more than 41 wt % (Evatane 42-60) (0.1 g), polyvinyl acetate 500000 MW (0.6 g) and cellulose (0.1 g, 20 μm). Polyurethane diol solution (0.6 g) was then added dropwise to the aerosol can along with the previously prepared solution of hydroxypropyl methylcellulose polymer powder (i.e. Methocel 311) in ethanol (9.95 g). The aerosol can was crimped and filled with dimethyl ether (70 g) at 5 bar pressure and a nozzle was attached.

We observed that both of Examples 9 and 10 yielded a spray jet of consistent force and quantity from a nozzle and the resulting coating was thin and translucent or transparent. In addition, they both exhibit a high level of hold to hair such that hair can be held in a particular position for prolonged periods of time without exhibiting stickiness.

The formulations listed in examples 11 and 12 were provided by mixing the stated raw materials. These possess the most desirable qualities for translucent/transparent hair styling sprayable compositions.

Example 11: Translucent or Transparent Sprayable Composition for Hair Styling

| Component | Ingredients | Quantity (g) | % w/w |
|---|---|---|---|
| Solvent | Ethanol | 9.95 | 12.17 |
| Propellant/solvent | Dimethyl ether | 70.00 | 85.68 |
| Binder | Polyvinyl acetate 500000 MW | 0.60 | 0.73 |
| Binder | A random copolymer of Ethylene and Vinyl acetate with a VA content of more than 41 wt % (Evatane 42-60) | 0.40 | 0.49 |
| Additive | Hydroxypropyl nnethylcellulose polymer powder (i.e. Methocel 311) | 0.05 | 0.06 |
| Additive | Polyurethane diol | 0.60 | 0.73 |
| Fibres | Cellulose, 20 μm | 0.05 | 0.06 |

Example 12: Translucent or Transparent Sprayable Composition for Hair Styling

| Component | Ingredients | Quantity (g) | % w/w |
|---|---|---|---|
| Solvent | Ethanol | 9.95 | 12.17 |
| Propellant/solvent | Dimethyl ether | 70.00 | 85.61 |
| Binder | Polyvinyl acetate 500000 MW | 0.60 | 0.73 |
| Binder | A random copolymer of Ethylene and Vinyl acetate with a VA content of more than 41 wt % (Evatane 42-60) | 0.40 | 0.49 |
| Additive | Hydroxypropyl methylcellulose polymer powder (i.e. Methocel 311) | 0.05 | 0.06 |
| Additive | Polyurethane diol | 0.60 | 0.73 |
| Fibres | Cellulose, 20 μm | 0.10 | 0.12 |

Method of preparation: As a preliminary step, 0.05 g of hydroxypropyl methylcellulose polymer powder (i.e. Methocel 311) was mixed with 9.95 g of ethanol thoroughly using a magnetic stirrer to create a solution of cellulose ether; this solution will henceforth be termed 'Solution A'.

To create both formulations 11 and 12, 0.4 g of a random copolymer of ethylene and vinyl acetate with a vinyl acetate content of more than 41 wt % (Evatane 42-60) and a ball bearing (optional) is first added to an empty 200 ml aerosol can. 0.6 g of polyvinyl acetate 500000 MW is then added to the can, followed by 0.05 g (Formula of the Example 11) or 0.1 g (Formula of the Example 12) of cellulose, 20 μm, 0.6 g of polyurethane diol, and 10 g of 'Solution A', in that order. A valve is then added to the can and the can crimped. The final step is to fill the can with 70 g of dimethyl ether at 5 bars of pressure and finish it by adding a nozzle.

Example 13: Sprayable Composition for Decorating Eyebrows

| Component | Ingredients | Quantity (g) | % w/w |
|---|---|---|---|
| Propellant | Dimethyl ether | 75 | 87.92 |
| Binder | A random copolymer of Ethylene and Vinyl acetate with 19 wt % to 42 wt % vinyl-acetate co-monomer (e.g. Evatane) | 1 | 1.17 |
| Binder | Polyvinyl acetate 500000 MW | 3 | 3.52 |
| Additive | Polyurethane diol | 4 | 4.69 |
| Additive | Silver bronze powder | 2 | 1.17 |
| Fibres | Cellulose, 20 μm | 0.3 | 0.35 |

Method of preparation: A ball bearing was added into a 200 mL aerosol can followed by a random copolymer of ethylene and vinyl acetate with 19 wt % to 42 wt % vinyl-acetate co-monomer (e.g. Evatane) (1 g), polyvinyl acetate 500000 MW (3 g), polyurethane diol (4 g), silver bronze powder (2 g) and cellulose, 20 μm (0.3 g). The aerosol can was crimped and filled with Dimethyl ether (75 g) at 5 bar pressure and a nozzle was attached.

Where Examples 5, 6, 7, 8, 9, 10, 11, 12 and 13 state "Cellulose, 20 μm" under the heading "Ingredients", this is in no way limited to that particular component, and can be substituted with other chemicals, as long as they are biological plant fibres, like milled cotton flock (e.g. a product code "CD60" from Goonvean Fibres Ltd). In terms of size, a range of 20-700 μm fibre size is acceptable. Any smaller will be detrimental to health if inhaled. However, it is preferred that cellulose, 20 μm be used for these formulations to obtain the best results. The size of the aerosol particles will very likely be larger than 20 μm because of the binders and additives coating the fibres.

An inlet pressure of 5 or 6 bars was initially used, along with a 0.5 valve, then later, a 0.33 valve. With the 0.5 valve it was discovered that the valve was blocked, so a 0.33 valve was used. The same type of nozzle, henceforth designated "S9", was used throughout the tests.

Pigments and colorants can be used to dye the formulations different colours, like e.g. dark gold, silver and superfine gold bronze powder (sourced from Tiranti), as well as powdered wax dyes in various colours (e.g. black, yellow, blue, green).

To qualitatively assess the aesthetic aspects of the formulations, such as the gloss, flexibility and the feel, initial tests were conducted on human hair (i.e. product name "Serenity Silky Straight", sourced from *Julia* Hair and Beauty and produced by J'adore) via spraying the samples directly with aerosol cans filled with different formulations. Each formulation can be distinguished by the presence or absence of certain components such as ethanol and PVA (e.g. polyvinyl acetate 500000 MW), affecting the aforementioned properties of the film. Both Examples 11 and 12 led to good spraying from a nozzle and the resulting coating was thin and translucent or transparent. Furthermore, the formulation of the Examples 11 and 12 exhibit also a high level of hold and rigidity to hair such that hair can be held in a particular position for prolonged periods of time without unnatural hardness, superior retention of shape in conditions of heat and humidity, and imparting thickness and body compared to current hairsprays.

Example 14: Humidity Test

Four hair samples (3 cm wide, 20 cm long) were curled and sprayed with four different hairsprays including:
1) Formulation 27
2) FBC100
3) Studio 2000
4) L'Oréal Elnett The hairsprays 1 and 2 are compositions of the present invention. Formulation 27 is the formulation as listed in the Example 9, and Formulation FBC100 is the formulation as listed in the Example 11.

The sample identified as Studio 2000 is the product in the market known as Studio 2000 System Professional Hairspray, and has the following ingredients: Alcohol denat, butane, propane, isobutane, water, octylacrylamide/acrylates/butylaminoethyl methacrylate copolymer, aminomethylpropanol, partum, diethyl phthalate, panthenol, citronellol, alpha-lsomethyl Ionone, and butylphenylmethylpropional. On the other hand, the sample identified as L'Oréal Elnett is the product in the market known as L'Oréal Paris Elnett Flexible Hold, and has the following ingredients: Alcohol denat, dimethyl ether, acrylates/T-butylacrylamide copolymer, polysilicone-8, aminomethyl propanol, limonene, linalool, benzyl salicylate, benzyl benzoate, alpha-isomethyl ionone, butylphenyl methylpropional, water, parfum/fragrance.

The samples were hung next to each other, as shown in FIG. 1, at standard ambient temperature and pressure (approximately 25° C. and 100 000 Pa or 1 bar), and approximately 50% RH, with the curls intact for all of the samples.

Figure 2:
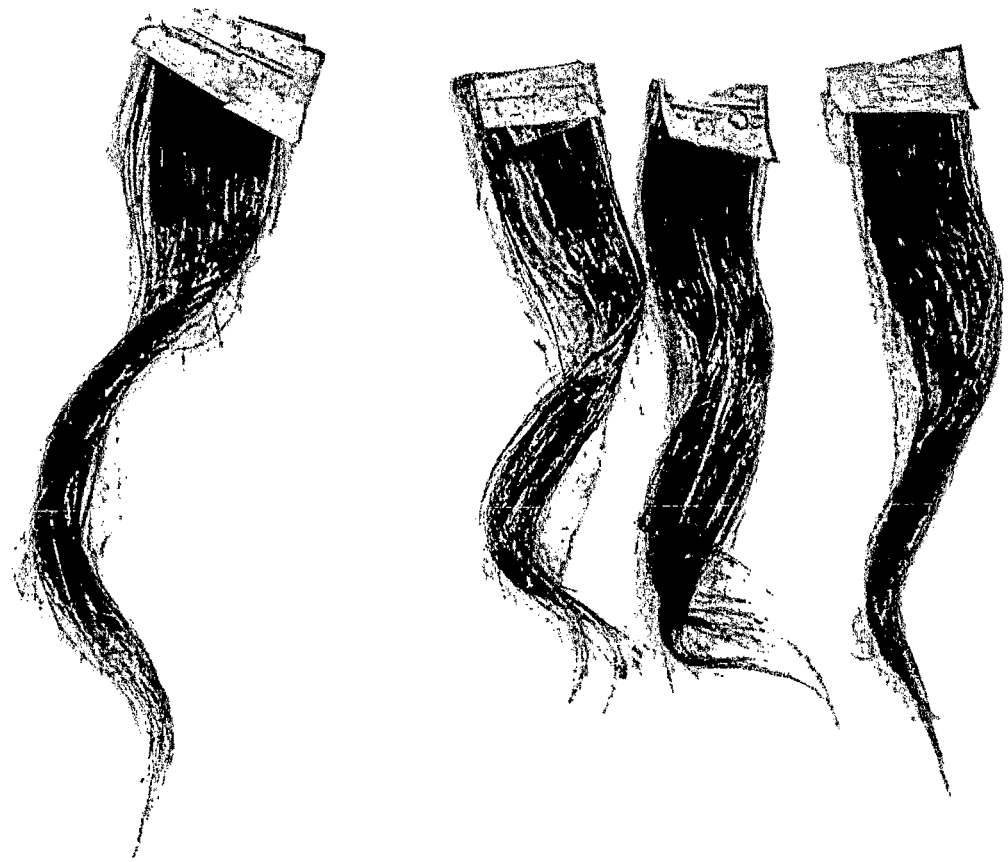
FIG. 2 illustrates the look of the four hair samples after the steam treatment, according to the Example 13.

The environment was then filled with steam produced by running hot water produced by a shower with a showerhead which is approximately 8 cm in diameter (at 3-5 bar) in a continuous stream in the close proximity of the samples (approx. 1.5 m away) for 30 minutes. The water flow was then stopped and the samples were allowed to hang for another 20 minutes before the picture in FIG. 2 was taken:

By comparison of the look of the samples before and after the steam treatment, as well as by comparing the pictures in FIG. 1 and FIG. 2, it is clear that the steam treatment has affected all of the samples, however to different degrees:

a) Judging by the elongation of the curl it appears that hair samples containing Formulation FBC100 (Example 11), and Studio 2000 sprays have retained the length the best and hair samples containing L'Oréal Elnett and Formulation 27 (Example 9) were less effective in length retention.

b) Judging by the hold of the shape of the curl the samples containing L'Oreal Elnett and Studio 2000 hair sprays were observed to have inferior degrees of strength when compared to Formulation 27 (Example 9) and even more so when compared to Formulation FBC100 (Example 11).

Based on these observations, it may be concluded that the hairspray containing FBC100 (Example 11) shows a superior hold of the hair in a styled position in comparison with the other three hairsprays analysed in this experiment. The stickiness created by humidity disappeared for all samples when they were removed from the steamy environment to a standard ambient temperature and pressure, and approximately 50% RH. Therefore, it is shown that the compositions of the invention exhibit equal or superior retention of the desired hairstyling shape in conditions of heat and humidity in comparison to previously known hairsprays.

Example 15: Comparison with Products on the Market

Three formulations of the invention were tested against two hairspray products obtained from the market. The test analysed the following:
1. Formulation FBC100
2. Formulation 27
3. Formulation 33
4. L'Oréal Elnett
5. Studio 2000

The hairsprays 1, 2 and 3 of this Example are compositions of the present invention. Formulation FBC100 is the formulation as listed in the Example 11, Formulation 27 is the formulation as listed in the Example 9 and Formulation 33 is the formulation as listed in the Example 5.

As mentioned above, the sample identified as 'Studio 2000' is the product in the market known as "Studio 2000 System Professional Hairspray", which has the following ingredients: Alcohol denat, butane, propane, isobutane, water, octylacrylamide/acrylates/butylaminoethyl methacrylate copolymer, aminomethylpropanol, parfum, diethyl phthalate, panthenol, citronellol, alpha-Isomethyl Ionone, and butylphenylmethylpropional; and the sample identified as 'L'Oréal Elnett' is the product in the market known as "L'Oréal Paris Elnett Flexible Hold", which has the following ingredients: Alcohol denat, dimethyl ether, acrylates/T-butylacrylamide copolymer, polysilicone-8, aminomethyl propanol, limonene, linalool, benzyl salicylate, benzyl benzoate, alpha-isomethyl ionone, butylphenyl methylpropional, water, parfum/fragrance.

Figure 3:
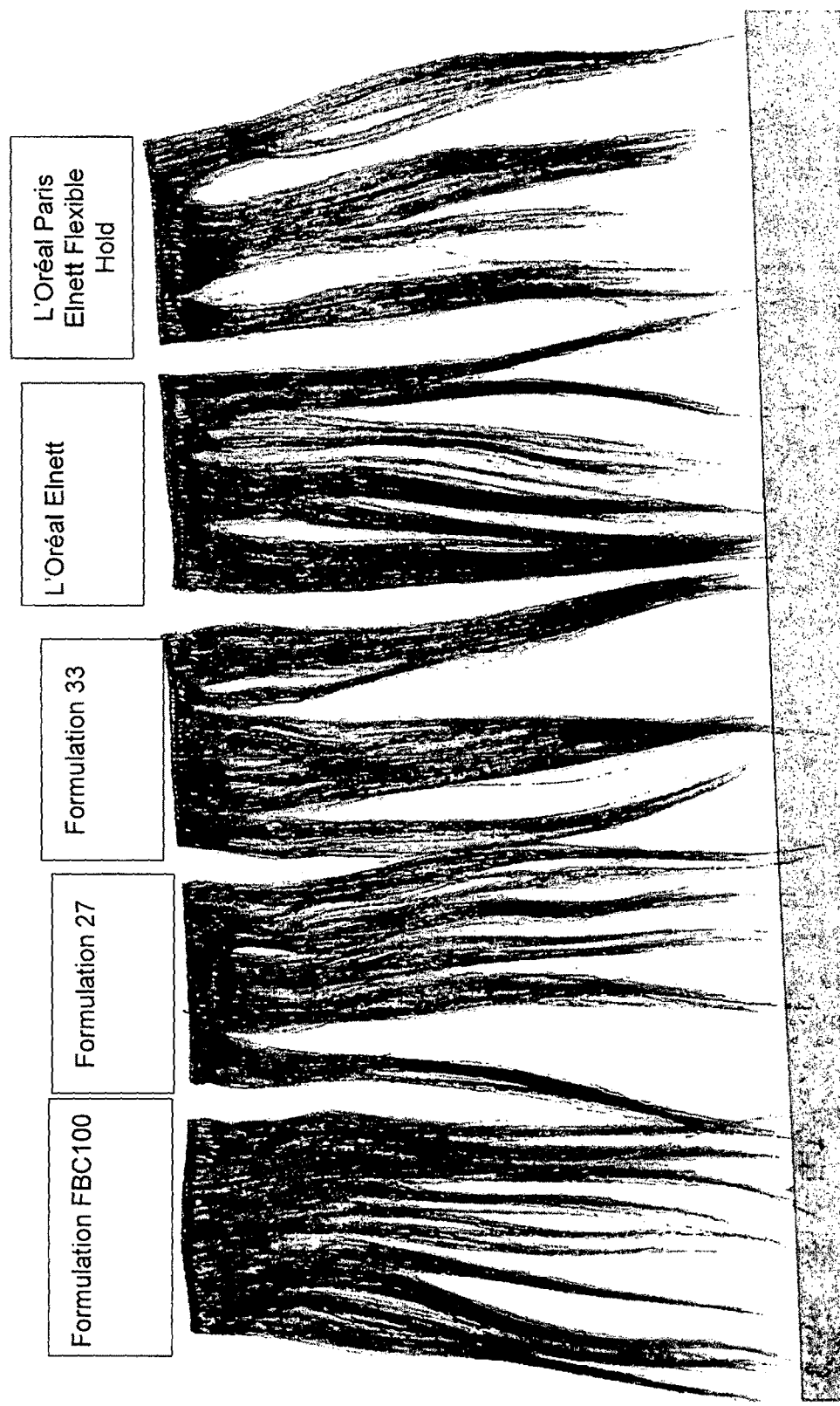
FIG. 3 illustrate the look of the samples of loose hair (8 cm wide 20 cm long) sprayed with five different products, according to the Example 14. From left to right, the first hair sample was sprayed with the hairspray identified herein as 'Formulation FBC100', which corresponds to the formulation as listed in the Example 11; the second hair sample was sprayed with the hairspray identified herein as 'Formulation 27', which corresponds to the formulation as listed in the Example 9; the third hair sample was sprayed with the hairspray identified herein as 'Formulation 33', which corresponds to the formulation as listed in the Example 5 the fourth hair sample was sprayed with the hairspray identified herein as 'L'Oréal Elnett', which corresponds to the product known as "L'Oréal Paris Elnett Flexible Hold"; and the fifth hair sample was sprayed with the hairspray identified herein as 'Studio 2000', which corresponds to the product known as "Studio 2000 System Professional Hairspray".
Figure 4:
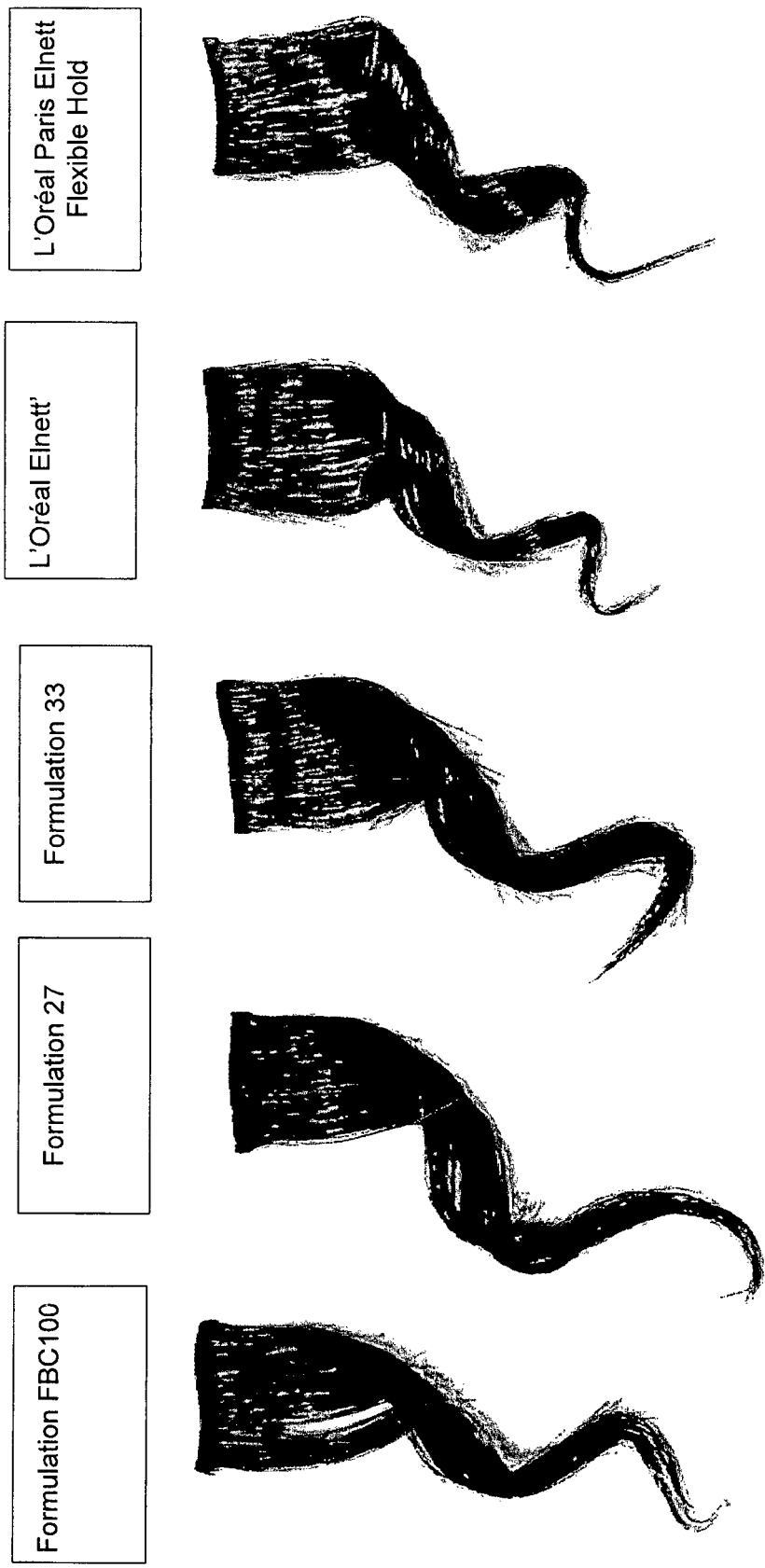
FIG. 4 illustrates the look of the samples of hair (4 cm wide 20 cm long) curled using a curling iron and then sprayed with five different products, according to the Example 14.

The tests were carried out in identical conditions:
The spray cans were all held 60 cm away from the hair swatch when spraying.
The spraying was continuous for the time of 4.5 seconds for every sample.
The spraying was carried out at room temperature at approximately 23° C.
The tests were also carried out on two different samples for each hairspray used, including:
a) 8 cm wide 20 cm long loose hair samples (FIG. 3).
b) 4 cm wide 20 cm long hair that were curled using a curling iron prior them being sprayed (FIG. 4).

By comparing the hair samples 1-5 of this Example from a visual perspective as well as by touch, it may be concluded that when identical hair samples are subjected to identical spray conditions listed above the compositions of the present invention (i.e. Formulation FBC100, Formulation 27 and Formulation 33) provide:

A more natural matte look than the compositions sprayed on the samples 4 (L'Oréal Elnett) and 5 (Studio 2000)
Increased hair volume compared to the compositions sprayed on the samples 4 (L'Oréal Elnett) and 5 (Studio 2000)
Increased hair thickening and fixing compared to the compositions sprayed on the samples 4 (L'Oréal Elnett) and 5 (Studio 2000)
A more natural dry touch feel than the compositions sprayed on the samples 4 (L'Oréal Elnett) and 5 (Studio 2000)

The hair sample 1 (sprayed with Formulation FBC100) and hair sample 4 (sprayed with L'Oréal Elnett) have also been subjected to thermal treatment by spraying two separate samples of hair on a mannequin head first and then curling them using a curling iron. This was performed in order to evaluate the differences after heating between the compositions of the present invention and the one readily available on the market.

After the heat treatment with the curling iron, the hair sample 1 sprayed with Formulation FBC100 (i.e. Example 11) displayed a glossier look in comparison to the curl that was heat treated before spraying the product (FIG. 4) while retaining the previously observed natural feel and look. In contrast, after imposing the same tests conditions using the composition sprayed on the sample 4 (i.e. L'Oréal Paris Elnett) the curl displayed an easily noticeable degree of unnatural hardness and an unnatural shine. Therefore, it is verified that the compositions of the present invention exhibit equal or superior retention of the desired hairstyling shape in conditions of heat in comparison to previously known hairsprays.

Example 16: Test of a Sprayable Composition of the Invention with Added Water Content The compatibility of the formulation FBC100 (i.e. Example 11) with added water content was tested. Four variants of the hair spray formulation FBC100 were produced by addition of increasing amounts of water to the mixture:
1. Formulation 83 (FBC100+2 g of tap water)
2. Formulation 90 (FBC100+1 g of tap water)
3. Formulation 91 (FBC100+0.5 g of tap water)
4. Formulation 92 (FBC100+0.25 g of tap water)

The following table summarizes the observations seen when the four formulations above were sprayed on hair samples:

| Formulation | Small amount sprayed (0.03 g-0.05 g of product once dry) | Large amount sprayed (0.07 g-0.09 g of product once dry) |
| --- | --- | --- |
| Formulation 83 | Hair clumping or agglomeration observed which were not the case for waterless formulation FBC100 | Hair stuck together very strongly and a lot more so than for waterless formulation FBC100 |
| Formulation 90 | Very slight hair clumping but a lot less so than for Formulation 83. The distribution of the composition is not as fine as for FBC100 but very close to it. | Hair stuck together, but less than for Formulation 83. |
| Formulation 91 | A very similar effect to that of formulation FBC100 with the distribution of the composition on the hair being slightly less fine. | Hair stuck together in clumps similarly to formulations 83 and 90. Distribution of the composition is not fine. |
| Formulation 92 | Hardly distinguishable from FBC100. | Hardly distinguishable from FBC100. |

It appears water slightly inhibits fine distribution of the composition when large amounts of it is sprayed, in the case of formulations 83, 90 and 91. However, as seen for formulations 90, 91 and 92, when small amounts of product are sprayed, the addition of up to 1 g of water to formulation FBC100 does not have a significant adverse effect on the appearance of the hair.

Results obtained for formulation 92 suggest that if water is used up to the amount of 0.25 g, large amounts of product can be sprayed without changing the effect seen for waterless formulation FBC100.

It may thus be concluded that water can be used with the compositions of the invention, such as formulation FBC100, but up to the amount of 1 g. More preferably up to 0.5 g and even more preferably up to 0.25 g.

Example 17: Test of a Sprayable Composition of the Invention with Added Oil Content and Perfume The compatibility of the formulation FBC100 (i.e. Example 11) with added oil content was tested.

Two variants of the key hair spray formulation FBC100 were produced:
1. Formulation 84 (FBC100+0.1 g Almond Blossom and Raspberry perfume oil)
2. Formulation 86 (FBC100+0.1 g PMX-200 Silicon Oil Fluid)

Results: In case of formulation 84, the effect on the hair remained the same except for the fact that the hair samples had a smell of perfume. In case of formulation 86 the silicone oil had no apparent effect on the formulation FBC100.

It may thus be concluded that oils and/or perfumes can be used with the compositions of the invention, such as formulation FBC100.

Example 18: Test of a Sprayable Composition of the Invention with Added Dyed Fibres As a comparison to using liquid/powder dyes as additives in the compositions of the invention, we investigated whether we can achieve the same effect by using fibres that have been previously dyed. To do this we produced the following four formulations:
1. Formulation 85 (FBC100 (i.e. Example 11)+0.05 g yellow Nylon fibres RILSAN Yellow 7391ES)
2. Formulation 87 (FBC100+0.05 g cellulose 20 μm+0.05 g yellow Nylon fibres RILSAN Yellow 7391ES)
3. Formulation 88 (FBC100+0.1 g yellow Nylon fibres RILSAN Yellow 7391ES)
4. Formulation 89 (FBC100+0.2 g yellow Nylon fibres RILSAN Yellow 7391ES)

When each of the formulations 1-4 were sprayed on hair the samples showed no significant difference in respect of shaping hold or colour when compared to the formulation FBC100. Subsequently, the formulations were sprayed on white paper to see whether the addition of yellow Nylon fibres had any effect to the formulation FBC100:
For both formulation 85 and formulation 87 a transparent film with a faint yellow tinge was produced
Formulation 88 produced a transparent film with a visible coloration of yellow, stronger than for formulations 85 and 87
Formulation 89 produced a transparent film with an even stronger yellow coloration than that seen in formulation 88

Although the colour from the fibres was not visible on hair, this may be a result caused by the choice of testing the colour yellow which, when dispersed over a fine film on the hair, becomes camouflaged by the colour of the hair. This demonstrates that dyed fibres may be used to achieve coloring effects, as it provides an alternative to using liquid/powder dyes in combination with the propellant and solvent used in the other formulations.

The invention claimed is:

1. A sprayable composition comprising a propellant and at least one binder being an ethylene vinly alkanoate copolymer, characterised in that the ethylene vinyl alkanoate copolymer is a random copolymer of ethylene and vinyl alkanoate having a vinyl acetate content within the range of 40 wt % to 42 wt %.

2. The sprayable composition of claim 1, wherein the propellant is present in an amount within the range of 80 wt % to 99 wt %.

3. The sprayable composition of claim 1, wherein the propellant is selected from dimethyl ether, liquefied petroleum gas, or a combination thereof.

4. The sprayable composition of claim 1, wherein the composition further comprises a solvent.

5. The sprayable composition of claim 1, wherein the composition further comprising an additive selected from the group consisting of dyes, oils, perfumes, surfactants, fire retardants, metal powders/particles such as copper, silver and gold, conditioners such as humectants, sunscreen, moisturisers, acidifiers, lubricants, preservatives, antistatic agents, and wax.

6. The sprayable composition of claim 1, wherein the composition further comprising fibres.

7. A method for forming a coating on a surface, the method comprising:
(i) spraying the composition of claim 1 on to the surface; and
(ii) allowing the propellant in the composition sprayed on the surface to evaporate.

8. The method according to claim 7, wherein the surface is human or animal hair.

9. A method for styling hair, the method comprising:
(i) spraying the composition of claim 1 on hair;
(ii) styling the hair; and
(iii) allowing the propellant to evaporate.

* * * * *